United States Patent
Punja

[11] 4,000,180
[45] Dec. 28, 1976

[54] PROCESS FOR PREPARING 2-DIHALOVINYL-3,3-DIMETHYL CYCLO PROPANE DERIVATIVES

[75] Inventor: Nazim Punja, Wokingham, England

[73] Assignee: Imperial Chemical Industries Limited, London, England

[22] Filed: Aug. 4, 1975

[21] Appl. No.: 601,495

[30] Foreign Application Priority Data

Aug. 14, 1974  United Kingdom ............ 35751/74
May 16, 1975  United Kingdom ............ 20885/75

[52] U.S. Cl. .......................... 260/468 H; 260/464; 260/586 R; 260/648 R
[51] Int. Cl.² ..................................... C07C 120/00
[58] Field of Search ........... 260/468 H, 464, 648 R, 260/586 R

[56] References Cited
UNITED STATES PATENTS

| | | | |
|---|---|---|---|
| 3,077,496 | 2/1963 | Julia | 260/468 H X |
| 3,354,196 | 11/1967 | Julia | 260/465.4 X |
| 3,761,505 | 9/1973 | Julia | 260/464 |
| 3,786,052 | 1/1974 | Martel et al. | 260/648 R X |

*Primary Examiner*—Joseph Paul Brust
*Attorney, Agent, or Firm*—Cushman, Darby & Cushman

[57] ABSTRACT

A process for the preparation of a compound of formula:

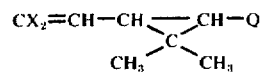

wherein X is chlorine or bromine, and Q is selected from the group consisting of cyano, acetyl and alkoxycarbonyl which comprises the step of heating a compound of formula:

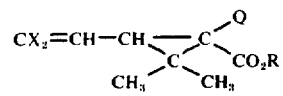

wherein R is a lower alkyl group, for a period of from one to 30 hours, at a temperature in the range 130° to 200° C in a polar aprotic solvent in the presence of at least two molar equivalents of water.

10 Claims, No Drawings

PROCESS FOR PREPARING 2-DIHALOVINYL-3,3-DIMETHYL CYCLO PROPANE DERIVATIVES

The present invention relates to a process for the preparation of valuable chemical intermediates.

2(2,2-Dichlorovinyl) -3,3-dimethylcyclopropane carboxylic acid is an important intermediate in the production of insecticides, including for example, 3-phenoxybenzyl 2(2,2-dichlorovinyl)-3,3-dimethyl-cyclopropane carboxylate. The preparation of 2(2,2-dichlorovinyl)-3,3-dimethylcyclopropane carboxylic acid has been described by Farkas et al (Collection Czechoslov. Chem. Commun., (1959), 24, pp 2230-2236) by the reaction of ethyl diazoacetate with 1,1-dichloro-4-methyl-1,3-pentadiene followed by hydrolysis of the resultant ethyl ester. This process is not suitable for large scale preparation of the acid because of the difficulties of working with ethyl diazoacetate, which is a substance which can explosively decompose unless the conditions are rigorously controlled, and which is believed to be a potent carcinogen.

We have now discovered that it is possible to prepare the above acid by a process which does not involve the use of diazoacetate. The initial stages of this process are set out in our copending UK patent application Nos. 20884/75 and 20893/75.

According to the present application a process for the preparation of a compound of formula:

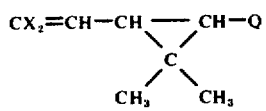

wherein X is chlorine or bromine, and Q is an electrowithdrawing group capable of conversion to a carboxyl group by hydrolysis, oxidation, or otherwise, which comprises the step of heating a compound of formula:

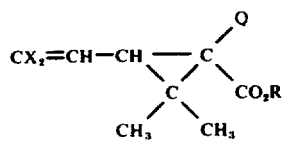

where R is an alkyl group, for a period of from 1 to 30 hours at a temperature in the range 130° to 200° C in a polar aprotic solvent in the presence of at least 2 molar equivalents of water.

Examples of compounds which may be prepared by the process of the invention are those wherein Q is a cyano, alkoxycarbonyl, acetyl or trihalomethyl group, which may readily be converted to the corresponding carboxylic acid.

Suitable polar aprotic solvents include for example dimethylsulphoxide, dimethylformamide and dimethylacetamide.

The progress of the invention process may be accelerated if certain ionic metal salts are present, particularly metal halides or metal cyanides. Preferred metal salts are those which readily ionise and dissolve to some extent in the polar aprotic solvent, for example alkali metal halides such as sodium chloride, sodium bromide or sodium iodide, or alkali metal cyanides such as sodium cyanide or potassium cyanide.

Although the exact period of heating will vary according to the nature of the starting material, a period of from 5 to 20 hours will usually give a satisfactory yield of the desired product. Preferably the heating is carried out under an inert atmosphere to minimise thermally stimulated oxidative degradation of the starting material or product.

Using the process of the invention various precursors of the desired acids may be obtained, for example:

ethyl 2(2,2-dichlorovinyl)-3,3-dimethylcyclopropane 1-carboxylate may be obtained from ethyl 1-ethoxycarbonyl -2(2,2-dichlorovinyl)-3,3-dimethylcyclopropane 1-carboxylate;

methyl 2(2,2-dibromovinyl)-3,3-dimethylcyclopropane carboxylate may be obtained from methyl 1-methoxycarbonyl-2(2,2-dibromo-vinyl)-3,3-dimethyl-cyclopropane l-carboxylate;

1-cyano-2(2,2-dichlorovinyl)-3,3-dimethylcyclopropane may be obtained from ethyl 1-cyano-2(2,2-dichlorovinyl)-3,3-dimethylcyclopropane 1-carboxylate;

1-acetyl-2(2,2-dichlorovinyl)-3,3-dimethylcyclopropane may be obtained from ethyl 1-acetyl-2(2,2-dichlorovinyl)-3,3-dimethylcyclopropane 1-carboxylate.

The invention is illustrated by the following example.

EXAMPLE

This example illustrates the preparation of ethyl 2(2,2-dichlorovinyl)-3,3-dimethylcyclopropane carboxylate from the corresponding gem-diethyl dicarboxylate. A mixture of diethyl 2(2,2-dichlorovinyl)-3,3-dimethyl-1,1-cyclopropane dicarboxylate (5.0g), sodium chloride (0.95 g), dimethylsulphoxide (12.0 ml) and water (0.6 ml) was heated under a nitrogen atmosphere to 175° C and maintained at that temperature for a period of 9 hours. At the end of this time the mixture was cooled to the ambient temperature and poured into water (50 ml). The mixture was extracted with petroleum ether (boiling range 60° to 80° C) and the extracts dried over anhydrous magnesium sulphate. After removal of the solvent by evaporation under reduced pressure the residual oil was subjected to purification by distillation and ethyl (2-(2,2-dichlorovinyl)-3,3-dimethylcyclopropane carboxylate was obtained as a colourless liquid (b.p. 102° C/13.3 Pa), and its identity confirmed by comparison of its n.m.r. and infra-red spectra with those of an authentic sample.

I claim:

1. A process for the preparation of a compound of formula:

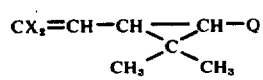

wherein X is chlorine or bromine, and Q is selected from the group consisting of cyano, acetyl and alkoxycarbonyl which comprises the step of heating a compound of formula:

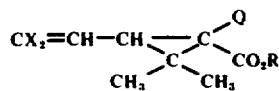

wherein R is a lower alkyl group, for a period of from one to 30 hours, at a temperature in the range 130° to 200° C in a polar aprotic solvent in the presence of at least two molar equivalents of water.

2. A process as claimed in claim 1 wherein the polar aprotic solvent is dimethylsulphoxide, dimethylformamide or dimethylacetamide.

3. A process as claimed in claim 1 and carried out in the presence of an alkali metal halide or alkali metal cyanide.

4. A process as claimed in claim 3 in which the alkali metal halide is sodium chloride, sodium bromide or sodium iodide.

5. A process as claimed in claim 3 in which the alkali metal cyanide is sodium cyanide or potassium cyanide.

6. A process as claimed in claim 1 in which the period of heating is in the range 5 to 20 hours.

7. A process as claimed in claim 1 in which the heating is carried out under an inert atmosphere.

8. The process of claim 1 wherein Q is $-CO_2R$, R being alkyl.

9. The process of claim 8 wherein R is ethyl and X is chlorine.

10. The process of claim 9 wherein the solvent is dimethyl sulphoxide and the heating is carried out in the presence of sodium chloride.